United States Patent [19]

Weis

[11] 4,151,210
[45] Apr. 24, 1979

[54] PROCESS FOR THE PRODUCTION OF PHENYLALKYL SULPHONES

[75] Inventor: Claus D. Weis, Pfeffingen, Switzerland

[73] Assignee: Ciba-Geigy Corporation, Ardsley, N.Y.

[21] Appl. No.: 914,652

[22] Filed: Jun. 12, 1978

[30] Foreign Application Priority Data

Jun. 23, 1977 [CH] Switzerland .................. 7720/77
Jul. 20, 1977 [CH] Switzerland .................. 9000/77

[51] Int. Cl.² .......................................... C07C 147/06
[52] U.S. Cl. ............................................ 260/607 AR
[58] Field of Search .............................. 260/607 AR

[56] References Cited

FOREIGN PATENT DOCUMENTS 1359602 3/1964 France .................. 260/607 AR

OTHER PUBLICATIONS

Theilheimer, *Synthetic Methods of Organic Chemistry*, Basel-S. Karger Publishers, N.Y., vol. 2, #562, vol. 8, #681, vol. 13, #7.

*Primary Examiner*—Elbert L. Roberts
*Assistant Examiner*—Molly C. Eakin
*Attorney, Agent, or Firm*—Prabodh I. Almaula

[57] ABSTRACT

Phenylalkyl sulphones of the formula

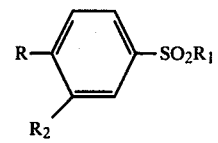

wherein

R represents hydrogen, halogen or alkyl of 1 to 4 carbon atoms, $R_1$ represents alkyl of 1 to 4 carbon atoms, and $R_2$ represents hydrogen, and, if R is hydrogen, or alkyl, also represents nitro, are obtained by reaction of a corresponding sulphinic acid derivative or a salt thereof with a dialkyl alkanephosphonate.

8 Claims, No Drawings

PROCESS FOR THE PRODUCTION OF PHENYLALKYL SULPHONES

The present invention relates to a process for the production of phenylalkyl sulphones.

The use of dimethyl methanephosphonate for the quaternation of basic dyes (cf. German Offenlegungsschrift No. 2,533,428) and for the methylation of nitrogen heterocyclic compounds containing a ring NH group [cf. Bull. Chem. Soc. Japan 49, 283–284 (1976)] is known from the literature.

It has now been found that aromatic sulphinic acids, and especially the salts thereof, can be very easily alkylated with dialkyl alkanephosphonates in good yields.

The process of the invention for the production of phenylalkyl sulphones of the formula

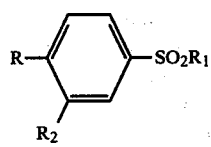
(1)

wherein

R represents hydrogen, halogen or alkyl of 1 to 4 carbon atoms, $R_1$ represents alkyl of 1 to 4 carbon atoms, and $R_2$ represents hydrogen and, if R is hydrogen or alkyl, also represents nitro, comprises reacting a sulphinic acid derivative of the formula

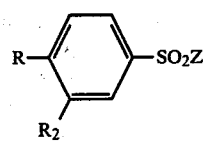
(2)

wherein R and $R_2$ have the above meanings and Z represents hydrogen or a salt-forming cation, with a dialkyl alkanephosphonate of the formula

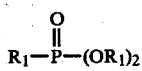
(3)

wherein $R_1$ has the above meaning.

Suitable sulphinic acid derivatives are both hydrated and anhydrous salts, especially alkali metal salts.

Halogen is for example fluorine, chlorine or bromine, preferably chlorine, and a salt-forming cation can be an alkali metal, ammonium or amine salt ion, preferably the sodium and potassium ion.

The reaction can be carried out in the presence or absence, but preferably in the presence, of a base.

Preferred bases are alkali metal carbonates and bicarbonates, for example those of sodium and potassium; tertiary amines, for example trialkylamines, preferably triethylamine; or trialkanolamines, preferably triethanolamine, or mixtures of such bases.

The process of the invention can be carried out under pressure or without pressure, but preferably under pressure. In this connection, the term "pressure" is to be understood as meaning the autogenous pressure which forms in the autoclave.

The reaction temperatures are from 130° to 190° C., preferably from 150° to 170° C.

A particularly interesting process is that for the production of phenylalkyl sulphones of the formula

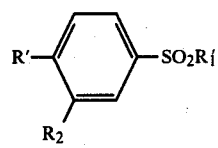
(4)

wherein

R' represents hydrogen, chlorine, methyl or ethyl, $R'_1$ represents methyl or ethyl, and $R_2$ represents hydrogen and, if R' is hydrogen, methyl or ethyl, also represents nitro, which comprises reacting a sulphinic acid derivative of the formula

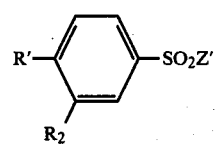
(5)

wherein R' and $R_2$ are as defined in formula (4) and Z' represents an alkali metal ion, with a dialkyl alkanephosphonate of the formula

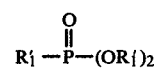
(6)

wherein $R'_1$ is as defined in formula (4), as well as that for the production of 4-chlorophenylmethylsulphones of the formula

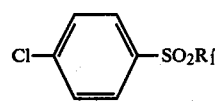
(7)

wherein $R'_1$ represents methyl or ethyl, which comprises reacting a sulphinic acid derivative of the formula

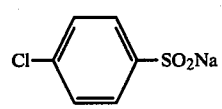
(8)

with a dialkyl alkanephosphonate of the formula

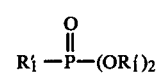
(6)

wherein $R'_1$ is as defined in formula (4).

A preferred process is that for the production of the phenylalkyl sulphone of the formula

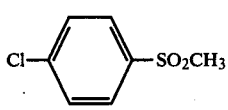
(9)

which comprises reacting the sulphinic acid derivative of the formula (8) with the dialkyl alkanephosphonate of the formula

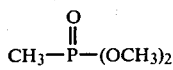
(10)

The phenylalkylsulphones which are obtainable according to the present invention are valuable intermediates for the production of fluorescent brightening agents and dyestuff intermediates (cf. U.S. Pat. No. 3,378,389 and British patent specification No. 1,118,745).

The addition of bases, as defined hereinabove, not only increases the yield, but also the purity of the phenylalkylsulphones obtained.

The invention is illustrated by the following Examples, in which the parts are by weight.

EXAMPLE 1

A 500 ml capacity steel autoclave, equipped with stirrer, is charged with 102 g of 74.5% hydrated sodium 4-chlorophenylsulphinate, 36.2 g of sodium bicarbonate and 150 ml of dimethyl methanephosphonate and the mixture is heated for 1 hour to 170° C. After cooling, 150 ml of water are added and the thick, white, crystalline suspension is poured into 1 liter of water (pH 2.2). The batch is stirred and the precipitate is collected by filtration, washed with 1 liter of water, and dried at 55° to 60° C./30 torr in a drying cabinet, affording 68.1 g (95.3% of theory) of 4-chlorophenylmethylsulphone of the formula

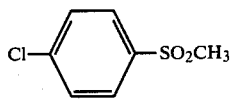
(100)

with a melting point of 94°–95° C. and a purity of 99%.

EXAMPLE 2

A 350 ml capacity sulphonating flask, equipped with stirrer, thermometer and reflux cooler, is charged with 27 g of 92% anhydrous sodium 4-chlorophenylsulphinate, 11 g of sodium bicarbonate, 50 ml of dimethyl methanephosphonate and 2.52 g of triethylamine, and the mixture is stirred. The oil bath is then heated to 190° C. in the course of 30 minutes, whereupon the internal temperatures rises to 158°–159° C. This temperature is kept for a further 70 minutes, then the heating bath is removed, and the contents of the flask are cooled to 30° C. The yellow suspension is added to 400 ml of water and, after stirring for 2 hours, the crystalline product is collected on a suction filter and washed with 500 ml of water, then dried at 50°–60° C./30 torr in a drying cabinet, affording 21.9 g to 22 g (92.2% of theory) of the product of the formula (100) with a melting point of 93°–95° C. and a purity of 98%.

EXAMPLE 3

A 350 ml capacity sulphonating flask, equipped with stirrer, thermometer and descending cooler, is charged with 34 g of 73% sodium 4-chlorophenylsulphinate (hydrated product), 11 g of sodium bicarbonate and 50 ml of dimethyl methanephosphonate and the mixture is stirred. The flask is heated to a bath temperature of 171° C., in the course of which 11 ml of distillate are condensed. The descending cooler is then exchanged for a reflux cooler and a bath temperature of 175° C. is maintained for a further hour. After cooling to room temperature, working up is effected as described in Example 2. Yield: 20 g (83.9% of theory) of the product of the formula (100) with a melting point of 93°–95° C. and a purity of 95.1%.

EXAMPLE 4

To a suspension of 24.8 g of sodium 4-chlorophenylsulphinate (anhydrous, 92%) in 50 ml of dimethyl methanephosphonate are added 12.6 g of triethylamine and the mixture is heated for 10 minutes to 152°–155° C. After cooling to room temperature, working up is effected as described in Example 2. Yield: 21.7 g (91.6% of theory) of the product of the formula (100) with a melting point of 93°–95° C. and a purity of 96.9%.

EXAMPLE 5

To a suspension of 22.06 g of 4-chlorophenylsulphinic acid in 50 ml of dimethyl methanephosphonate are added 12.6 g of triethylamine and the mixture is heated for 5 to 6 minutes to a temperature of 142°–145° C. The dark brown solution is poured into 400 ml of water and the batch is stirred for 2 hours. The resulting crystalline product is collected by filtration and washed with 500 ml of water, affording 16.6 g (69.7% of theory) of the product of the formula (100) with a melting point of 84°–93° C. and a purity of 64.6%. Recrystallization from ethanol yields the pure product with a melting point of 94°–95° C.

EXAMPLE 6

A suspension of 24.8 g of sodium 4-chlorophenylsulphinate (92%, anhydrous) in 100 ml of dimethyl methanephosphonate is heated in the course of 10 minutes to 180° C. and kept for 20 minutes at this temperature. The reaction mixture is then poured into 750 ml of water. The precipitated crystalline product is collected by filtration, affording 15.25 g (62% of theory) of the product of the formula (100) in a purity of 64%. Recrystallisation from ethanol yields the pure product with a melting point of 94°–95° C.

EXAMPLE 7

A suspension of 22.7 g of sodium p-toluenesulphinate in 50 ml of dimethyl methanephosphonate is treated with 12.6 g of triethylamine and the mixture is heated in the course of 45 minutes to 167° C. The temperature is raised further to 171° C. and kept thereat for a further 30 minutes. The cooled solution is poured into 700 ml of water and stired for 1 hour. The precipitated crystalline product is collected by filtration and washed with 350 ml of water. The residue is dried at 25 torr and 50° C., affording 17.2 g (80.9% of theory) of p-tolylmethylsulphone of the formula

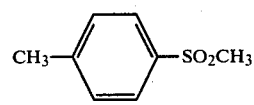
(101)

with a melting point of 85°–96° C. and a purity of 95.8%.

EXAMPLE 8

The procedure of Example 7 is repeated, using 20.5 g of sodium benzenesulphinate. Yield: 13.2 g (72.8% of theory) of phenylmethylsulphone of the formula

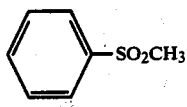

with a melting point of 82.5°-85° C. and a purity of 96.8%.

EXAMPLE 9

A 250 ml capacity sulphonating flask, equiped with stirrer, thermometer and cooler, is charged with 27 g of 92% anhydrous sodium 4-chlorophenylsulphinate, 10.5 g of sodium bicarbonate and 70 ml of diethyl ethylphosphonate. The mixture is stirred, then heated to 160° C. and volatile constituents are distilled off until the internal temperature has risen to 195° C. The batch is stirred at this temperature for 14 hours, then cooled, and the cooled solution is poured into 400 ml of water. The resulting white emulsion is stirred with 400 ml of diethyl ether and the ethereal solution is washed with three 250 ml portions of water, dried over sodium sulphate and concentrated. The residual oil is distilled at 103°-105° C./0.08 torr, affording 20.8 g (81.8% of theory) of 4-chlorophenylethylsulphone of the formula

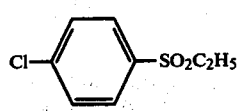

with a melting point of 42°-43° C. and a purity of 98%.

EXAMPLE 10

A 350 ml capacity sulphonating flask, equipped with a reflux cooler, thermometer and a descending cooler, is charged with 89 g of 42% sodium 3-nitrobenzenesulphinate (hydrated product), 17.6 g of sodium bicarbonate, 4.04 g of triethylamine and 100 ml of dimethyl methanephosphonate. The mixture is stirred, then heated to an internal temperature of 130° C. and volatile constituents are distilled off over a descending cooler until the internal temperature is 160° C. This temperature is maintained for a further 10 minutes, then the mixture is cooled to room temperature, poured into 800 ml of water and, after the addition of 3 ml of 28% aqueous ammonia solution, stirred for 10 minutes. The crude product is collected by filtration and extracted with 600 ml of methanol. The extract is concentrated to a volume of 300 ml and after cooling and suction filtration, 34.3 g (94.8% of theory) of 3-nitrophenylmethylsulphone of the formula

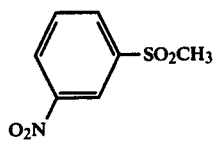

are obtained in the form of crystals which melt at 150°-150.5° C.

EXAMPLE 11

In accordance with the particulars of British patent specification No. 1,118,745, 90 g of the compound of the formula (100) are heated at reflux for 8 hours with 15.1 g of hydrazine. 22.3 g of the resulting (p-hydrazinophenyl)-methylsulphone of the formula

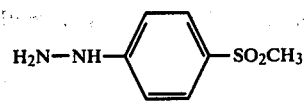

are charged into 400 ml of 50% ethanol, then 26 g of sodium carbonate are added and, with stirring, the mixture is treated at 70° to 75° C. in the course of 20 minutes with a solution of 20 g of p-chloro-ω-dimethylaminopropiophenone hydrochloride in 100 ml of 50% ethanol. The reaction mixture is then heated at reflux for 20 hours with stirring, then cooled. The pale yellow precipitate is collected by filtration, washed with ethanol and water, dried, and recrystallised from chlorobenzene, yielding the compound of the formula

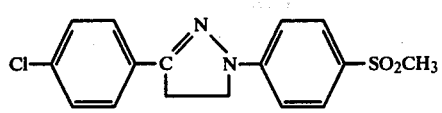

which can be used as a fluorescent brightening agent (cf. U.S. Pat. No. 3,378,389).

EXAMPLE 12

5.6 g of the compound of the formula (105) are heated at reflux with 4 g of ethyl acetate. Then 30 ml of ethanol and 6 ml of 10% sodium hydroxide solution are added and the mixture is stirred for 2 hours. The reaction mixture is acidified with acetic acid, affording 4.8 g of the compound of the formula

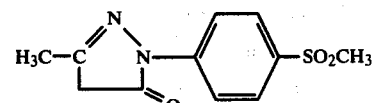

which can be used as magenta coupler (cf. British patent specification No. 1,118,745).

What is claimed is:
1. A process for the production of phenyalkyl sulphones of the formula

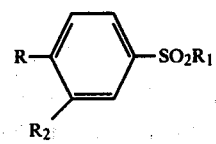

wherein
R represents hydrogen, halogen or alkyl of 1 to 4 carbon atoms,
$R_1$ represents alkyl of 1 to 4 carbon atoms and
$R_2$ represents hydrogen, and, if R is hydrogen or alkyl, also represents nitro, which comprises reacting a sulphinic acid derivative of the formula

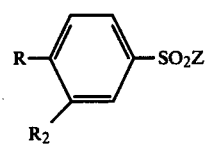

wherein R and $R_2$ are as defined above and Z represents hydrogen or a salt-forming cation, with a dialkyl alkanephosphonate of the formula

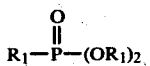

wherein $R_1$ is as defined above.

2. A process according to claim 1 for the production of phenylalkyl sulphones of the formula

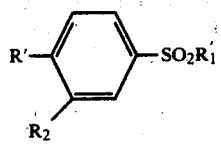

wherein

R' represents hydrogen, chlorine, methyl or ethyl,

R'$_1$ represents methyl or ethyl, and $R_2$ represents hydrogen, and, if R' is hydrogen, methyl or ethyl, also represents nitro, which comprises reacting a sulphinic acid derivative of the formula

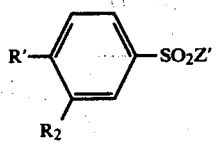

wherein R' and $R_2$ are as defined above, and Z' represents an alkali metal ion, with a dialkyl alkanephosphonate of the formula

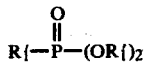

wherein R'$_1$ is as defined above.

3. A process according to claim 2 for the production of 4-chlorophenylalkyl sulphones of the formula

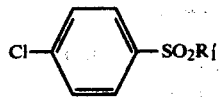

wherein R'$_1$ represents methyl or ethyl, which comprises reacting the sulphinic acid derivative of the formula

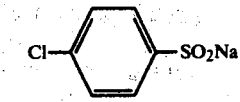

with a dialkyl alkanephosphonate of the formula

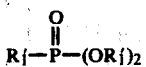

wherein R'$_1$ is as defined above.

4. A process according to claim 3 for the production of the phenylalkyl sulphone of the formula

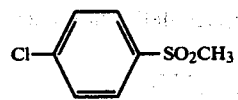

which comprises reacting the sulphinic acid derivative of the formula

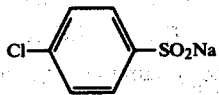

with the dialkyl alkanephosphonate of the formula

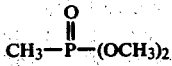

5. A process according to claim 1, wherein the reaction is carried out in the presence of a base.

6. A process according to claim 1, wherein the reaction is carried out under pressure.

7. A process according to claim 1, wherein the reaction is carried out in the presence of a base and under pressure.

8. A process according to claim 1, wherein an anhydrous or hydrated alkali metal salt of sulphinic acid is used as sulphinic acid derivative.

* * * * *